(12) United States Patent
Murphy (10) Patent No.: US 9,387,115 B2
(45) Date of Patent: Jul. 12, 2016

(54) COMPRESSIBLE BRAIDED MESH FINGER SPLINT AND THERAPEUTIC USES THEREOF

(71) Applicant: Joyce D. Murphy, Bloomfield Hills, MI (US)

(72) Inventor: Joyce D. Murphy, Bloomfield Hills, MI (US)

( * ) Notice: Subject to any disclaimer, the term of this patent is extended or adjusted under 35 U.S.C. 154(b) by 343 days.

(21) Appl. No.: 13/828,304

(22) Filed: Mar. 14, 2013

(65) Prior Publication Data

US 2014/0276309 A1 Sep. 18, 2014

(51) Int. Cl.
*A61F 5/00* (2006.01)
*A61F 5/10* (2006.01)
*A61F 5/058* (2006.01)

(52) U.S. Cl.
CPC ............... *A61F 5/10* (2013.01); *A61F 5/05875* (2013.01)

(58) Field of Classification Search
CPC ...... A01M 25/004; A61F 2/0805; A61F 5/04; A61F 2002/30331; A61F 2002/3037; A61F 2002/30387; A61F 2002/30397; A61F 2002/30398; A61F 2002/304; A61G 13/124; A61G 2013/0045; A61B 17/7026; A61B 17/7031; A61B 17/7043; A61B 17/7055; A61B 17/7068; A61B 17/7071; A61K 9/0024; A61K 47/32; A61K 47/34; A61K 47/36; A61K 47/42; A61L 17/005; A61L 31/16; A61L 2300/30; A61L 2300/40; A61L 2300/45; A61L 2300/404; A61L 2300/41; A61L 2300/432

USPC .................................. 602/20–22; 128/880
See application file for complete search history.

(56) References Cited

U.S. PATENT DOCUMENTS

| | | | | |
|---|---|---|---|---|
| 1,268,932 | A * | 6/1918 | Corrigan | 602/36 |
| 2,688,961 | A * | 9/1954 | Mazyck | 128/880 |
| 5,191,903 | A * | 3/1993 | Donohue | 128/879 |
| 5,451,203 | A * | 9/1995 | Lamb | 602/36 |
| 5,649,541 | A * | 7/1997 | Stuckey | 128/880 |
| 2004/0098095 | A1 * | 5/2004 | Burnside et al. | A61F 2/07 623/1.13 |

OTHER PUBLICATIONS http://www.boinks.com/our-products, internet website, date of publication unknown.
U.S. Appl. No. 13/828,304 disclose the BOINKS toy and website where the toy can be viewed and purchased, filing date of the present application.

* cited by examiner

*Primary Examiner* — Michael Brown
(74) *Attorney, Agent, or Firm* — Graham Curtin, P.A.

(57) ABSTRACT

A finger splint and method of providing support for a finger is disclosed. The finger splint can include a braided mesh folded over itself to form a hollow tube having a double wall and having a longitudinal axis. The folded over braided mesh can have a first open end that is flared. The braided mesh, before being folded over, is compressible and after being compressed and released, springs back to its original shape. In accordance with the method of providing support to a finger, a finger is inserted into an open end of a compressible tabular braided mesh splint that has been folded over to form a cylindrical two-walled splint and the splint is pulled onto the finger.

6 Claims, 9 Drawing Sheets

COMPRESSIBLE BRAIDED MESH FINGER SPLINT AND THERAPEUTIC USES THEREOF

BACKGROUND

The present invention relates to finger splints and to therapeutic uses of a compressible braided mesh.

A toy has previously been marketed under the name BOINKS. BOINKS toys are a tube formed of braided mesh. BOINKS are compressible along their longitudinal length and, when released, return to their original position. As a result of this property, BOINKS can be, and are, used as a toy that can be propelled in a direction opposite the direction of compression by first compressing and the releasing the toys.

It has recently been appreciated that the compressible braided mesh of BOINKS can be arranged in a novel configuration to provide new and improved therapeutic processes.

SUMMARY OF THE INVENTION

The present invention, in accordance with one embodiment, is a finger splint, having a braided mesh folded over itself to form a hollow tube having a double wall and having a longitudinal axis. In accordance with an aspect of the invention, the folded over braided mesh has a first open end that is flared. The braided mesh, before being folded over, is compressible and after being compressed and released, springs back to its original shape. The braided mesh folded over the splint is also compressible.

In accordance with an aspect of the present invention, the finger splint is compressed to receive a finger and released to support the finger. However, a finger can typically be inserted into the finger splint without further compression.

In accordance with an aspect of the present invention, the finger splint, when worn, allows the finger to be moved, while still providing some support.

In accordance with an aspect of the present invention, the splint, when worn, resists a movement of the finger.

In accordance with an aspect of the present invention, the finger splint is applied to treat a swollen, sprained, broken finger, or a finger that has been affected by a brain injury such as a stroke.

In accordance with an aspect of the present invention, the mesh is made of PET, also known as polyethylene terephthalate.

In accordance with an aspect of the present invention the braid is made of a textile composition made with yarn thread crossing in diagonal direction. Each thread intertwines the diagonal threads it crosses one from above and one from below. Braiding machines are used for such constructions. (see diagram of braid attached).

In accordance with an aspect of the present invention, the density of the mesh is as follows: The thickness of the final product ranges from 0.025"-1.0". Fibers of the braid range from 6 ml-16 ml depending on the construction of the braid.

In accordance with an aspect of the present invention, the finger splint is provided with a set of instructions providing guidance as to how to place the finger splint on a finger for therapeutic purposes and packaging encloses one or more finger splints and the set of instructions.

In accordance with another aspect of the present invention, a method of providing support to a finger is provided. The method includes the steps of inserting a finger into an open end of a compressible tabular braided mesh splint that has been folded over to form a cylindrical two-walled splint and the pulling the splint on the finger.

In accordance with another aspect of the present invention, an open end can be an end where the splint has been folded over.

In accordance with another aspect of the present invention, the open end can be flared.

DESCRIPTION

Figure 1:
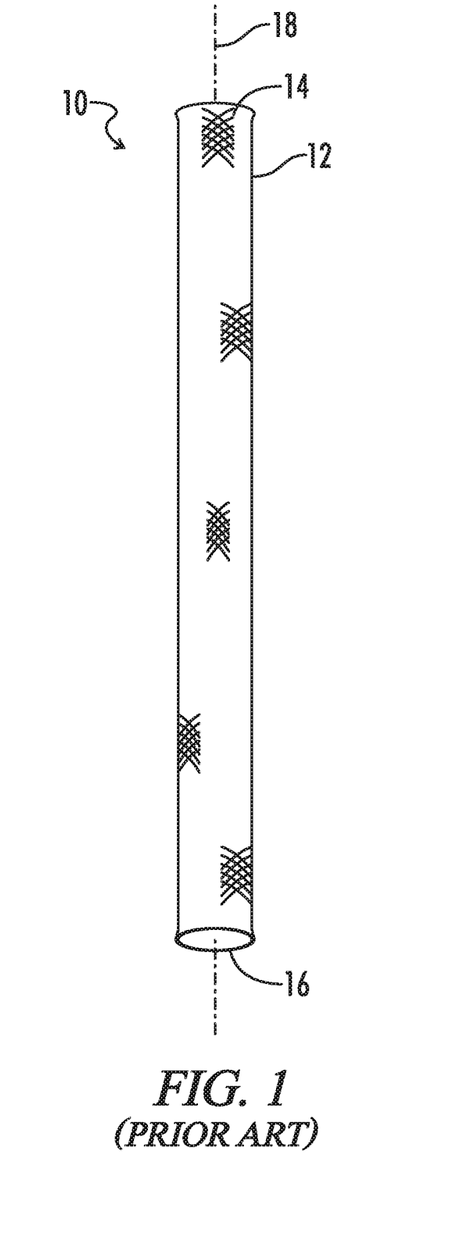
FIG. 1 illustrates a BOINKS prior art toy.

FIG. 1 shows a prior art toy 10. The toy 10 has been on the market for years. It has been marketed under the name BOINKS and can be viewed and purchased at www.boinks.com. The toy 10 is compressible along its length. When compressed and released, it shoots out. The toy 10 is soft and therefore provides a safe way for children to play.

The toy 10 is a braided mesh that forms a hollow tube 12 that has two open ends 14 and 16. The braid mesh tube is made from a plurality of fibers. The number of fibers used determines the circumference or diameter of the tube. The length of the fibers also determine the length of the tube 12. The fiber ends at the ends 14 and 16 of the tube 12 can be treated, for example, with heat or chemically, to fuse the fibers together. This helps maintain the integrity of the tube 12.

Any type of fiber can be used to form the tube 12. However, preferred fibers include PET. Other preferred fibers are polyester.

Figure 9:
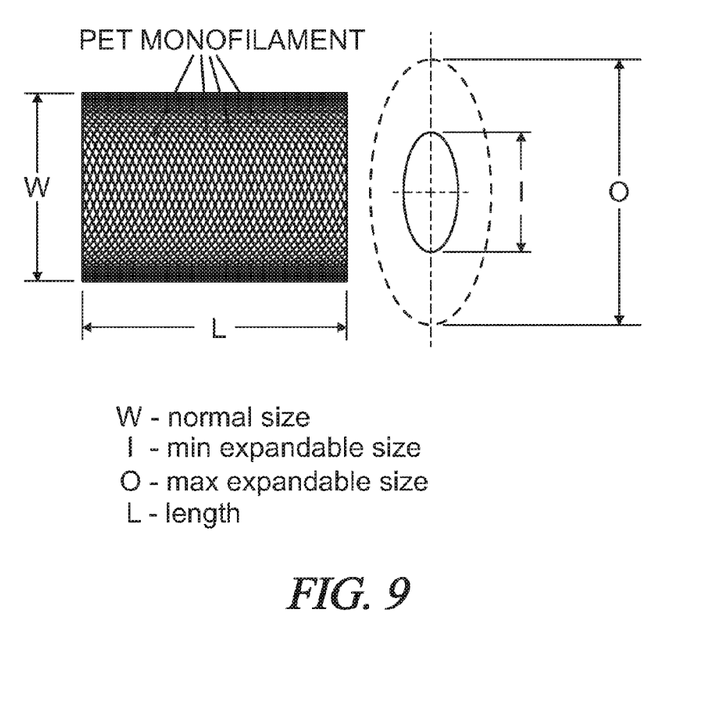
FIG. 9 illustrates the properties of the material the finger splint can be made from in accordance with aspects of the present invention.

The tube 12 can be formed by braiding the plurality of fibers. In accordance with one aspect of the present invention, the plurality of fibers are braided. The braid is made of a textile composition made with yarn thread crossing in diagonal direction. Each thread intertwines the diagonal threads it crosses one from above and one from below. Braiding machines are used for such constructions. FIG. 9 illustrates the operation of the braided tube in accordance with an aspect of the present invention.

The tube 12 thus formed, has a known property. The tube 12 is compressible along its tubular axis 18. Essentially, the open areas in the braided mesh tube become smaller when the toy is compressed. When released, the tube 12 expands along to tubular axis 18 and the toy 10 springs. Thus, the toy 12 is propelled along its tubular axis 18. This principal formed a basis to use the tube 12 as a toy 10.

However, a new use of the tube 12 has been invented. In accordance with one aspect of the present invention, the tube 12 is placed on a damaged finger to provide a finger split. The tube 12 can be compressed along its tubular axis prior to putting the tube splint on the finger. This compression causes the opening in the tube to become wider, thereby allowing the finger to be inserted into the tube easier. This can be helpful, particularly when the finger is swollen, or crooked This therapeutic use of the tube 12 provides support to a damaged finger, while allowing some flexibility of the finger. It has been found that alternate structural arrangements of the tube 12 can provide therapeutic benefit to damaged fingers.

The flexible finger splint is a braided device that can help with many types of inflictions. It is latex free, and when used in accordance with the present invention, provides light compression and mild extension support while allowing finger flexion.

The flexible finger splint can also be used to aid patients who have had a brain injury, stroke, Parkinson's, broken bone, Carpal syndrome, arthritis, and many other inflictions. The device can be placed on most all digits depending on size. It fits comfortable for longer wearing than other finger splints on the market.

The flexible finger splint of the present invention can be put in the dishwasher silverware holder for cleaning or hand washed. It is economical and can usually be reused depending on the use. It can be used by all ages. Children like to wear the flexible finger splint as opposed to the other splints on the market since it is comfortable and comes in fun colors. Adults find it more comfortable than the plastic types available and find they use it more for longer wearing.

Figure 2:
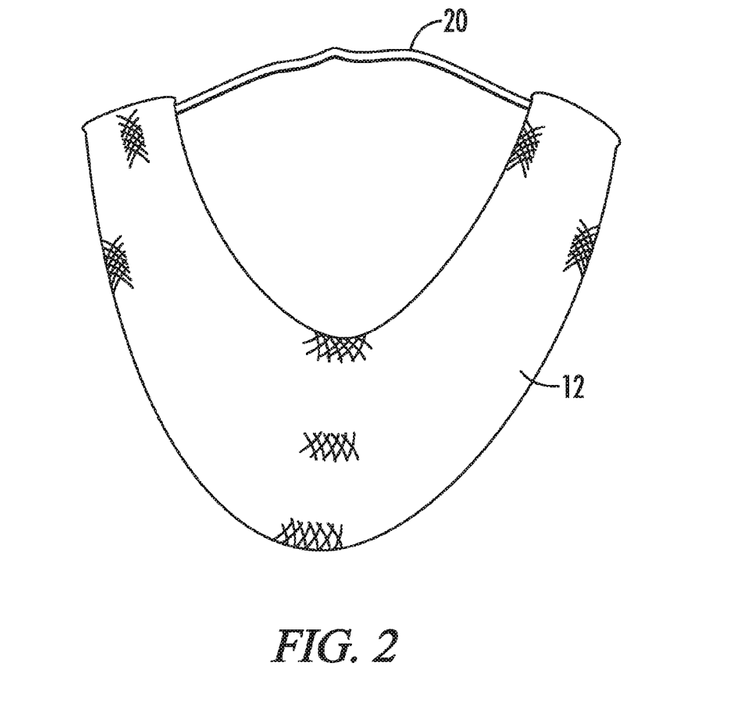
FIG. 2 shows a compressed BOINKS toy.
Figure 3:
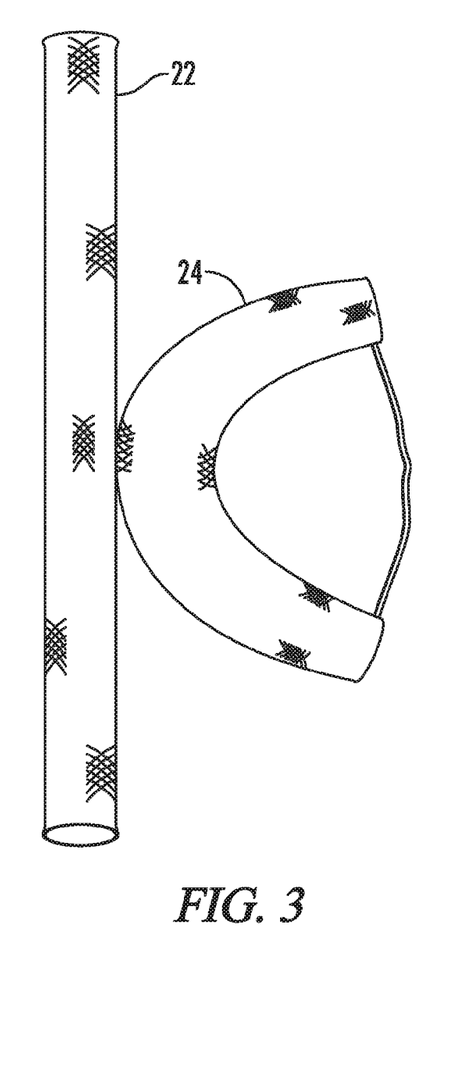
FIG. 3 shows a non-compressed braided mesh tube and a compressed braided mesh tube side by side.

FIG. 2 illustrates the tube 12 in a compressed state. The flexibility of the tube 12 is also illustrated by the bend in the tube 12. Note that the tube 12 is held in the compressed form by a wire 20, which is not part of the present invention. The tube 22 in its natural state and the compressed tube 24 are illustrated side by side in FIG. 3.

Figure 4:
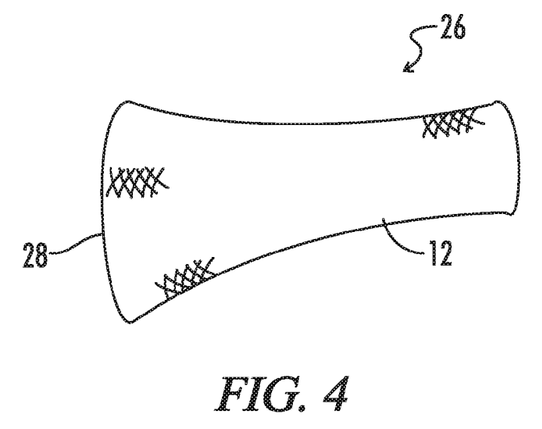
FIG. 4 shows a compressible elastic braided mesh arranged in a novel configuration to provide a finger splint.

FIG. 4 shows a compressible elastic braided mesh 26 arranged in a novel configuration to provide a finger splint. In FIG. 4, a tube 12, such as the one illustrated in FIG. 1, has been folded over itself to form a finger splint 26. The braided mesh walls of the tube 12 now form a double wall for the finger splint. The end 28 of the finger splint 26 where the fold was made is flared. This happens normally when the tube 12 is folded over on itself.

This arrangement makes it easier to place a finger in the open end 28 of the finger splint. The splint 26, as shown in FIG. 4, is still compressible. It still may be necessary to compress the splint 26 to insert a swollen finger into the splint 22. In other cases, it will not be necessary. Once the finger is inserted into the splint 26, the splint 26 can be pulled onto the finger by sliding the outside funnel down over itself to fit the finger.

The splint 26 of FIG. 4 forms a double walled braided mesh splint that provides added support for a damaged finger while still allowing some flexibility. The folded over end 28 of the splint 26 also provides protection for a patient because there is no open fiber end to rub against the skin.

Figure 5:
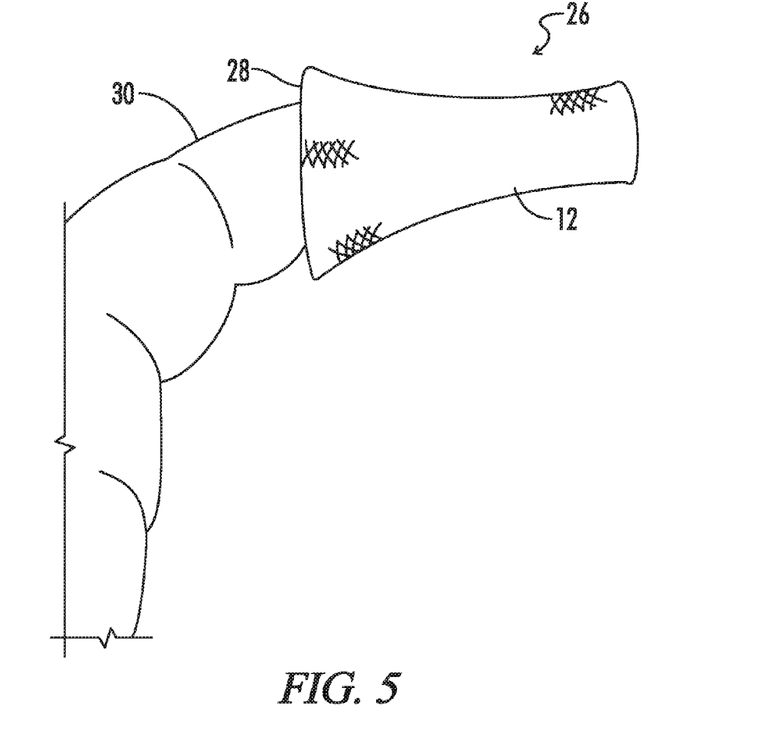
FIG. 5 shows the finger splint of FIG. 4 being applied to a finger to provide a therapeutic splint to the finger.

FIG. 5 shows the finger splint 26 of FIG. 4 being applied to a finger 30 to provide a therapeutic splint to the finger. As described before, the finger 24 is inserted into an open end 28 of the tubular finger splint 26. In accordance with one aspect of the present invention, the finger 30 is inserted into the flared end 28 of the tubular finger splint 26. This is the end of the tube that was folded into itself.

Figure 6:
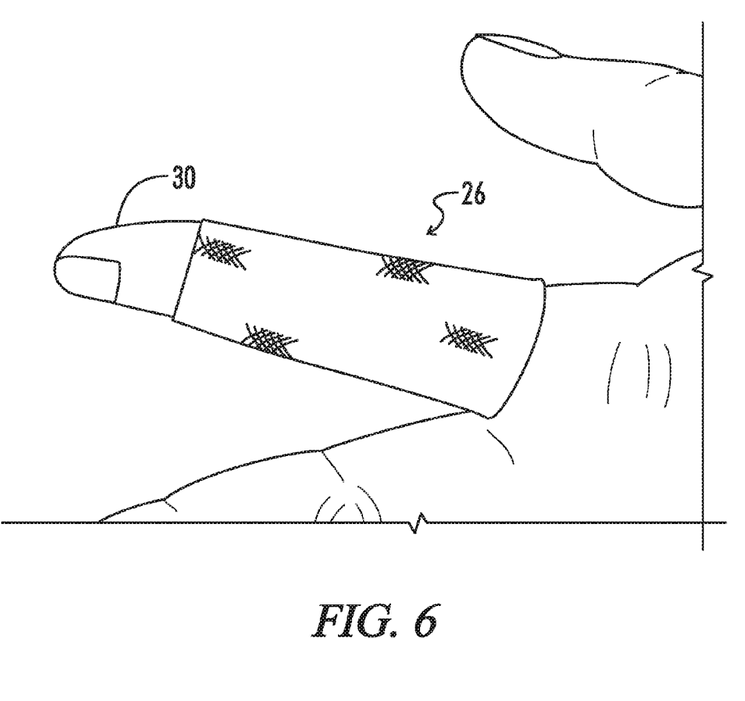
FIG. 6 shows the finger splint of FIG. 4 on a finger.

Once the finger 30 is inserted into the open end 28 of the tubular splint 26, the splint 26 is pulled onto the finger. FIG. 6 shows the finger splint of FIG. 5 pulled on a finger 30. When applied to a finger as shown in FIG. 6, the folded over compressible mesh tube provides support to a damaged finger. The amount of support can be controlled by the size of the tube, including its diameter.

Figure 7:
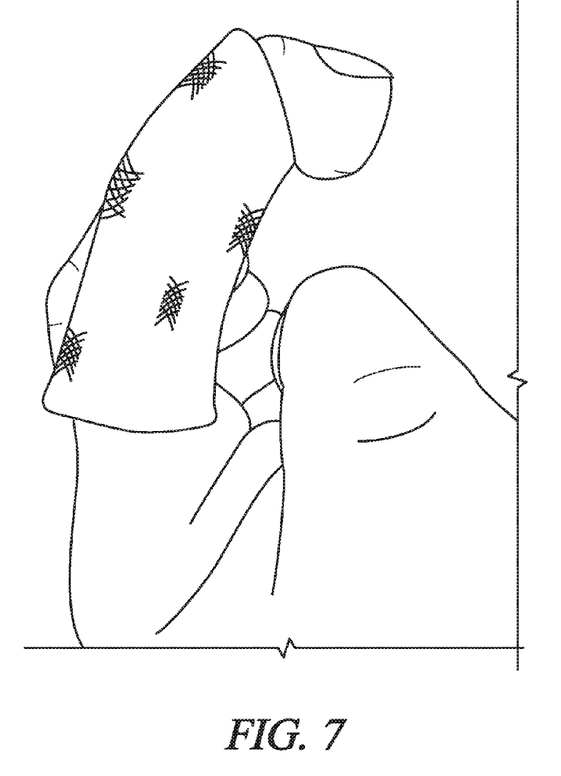
FIG. 7 shows a bent finger wearing the splint of FIG. 4.

The finger splint of the present invention is flexible to allow the finger to be moved but provides support to the finger during the movement. This is illustrated in FIG. 7, where a finger with the finger splint of the present invention is bent.

Figure 8:
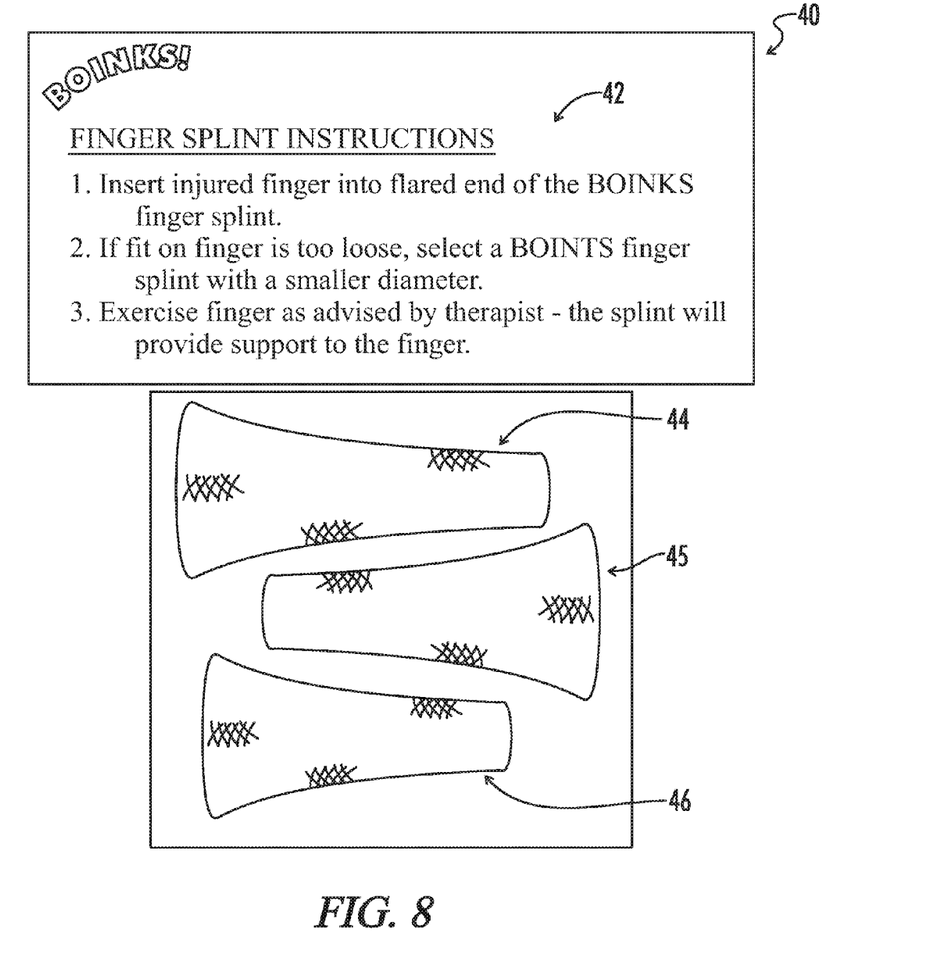
FIG. 8 illustrates the packaging and instructions provided with the finger splint in accordance with one aspect of the present invention.

In accordance with an aspect of the present invention, the finger splint shown in FIG. 4 is placed in packaging 40 with instructions 42 on how to use the structure as a splint. FIG. 8 shows the packaging 40 and instructions 42 provided with the finger splint. The folded over end of the splint is flared and the instructions can specify that the finger be inserted into the flared open end of the finger splint. In accordance with one aspect of the present invention, a plurality of splints 44-46 can be provided with packaging.

Alternatively, a variety of directions to apply the flexible finger splint can be provided: For example, "Place the funnel end over the finger you wish to immobilize, slide on all the way to your knuckle, adjust the splint by sliding the outside down toward the hand for a more snug fit. If the splint is too long for your hand, do not cut the braid as it will unravel. The Flexible Finger Splints comes in two large sizes: 5"×¾", 7"×¾" and one small size: 5"×½" for children and smaller hands."

The flexible finger splint can be provided in small, medium and large as well as custom sizes In accordance with another aspect of the present invention, the braided mesh shown in FIG. 1 can be placed in the packaging with the instructions to fold over one end of the splint upon itself as shown in FIG. 4, and that the finger is inserted into the folded over and flared end of the splint.

Therapists can also use the braided mesh tube in different types of therapy sessions. They can be used in treating patients with Autism, Parkinson's, brain injuries, strokes, and cerebral palsy. Here are a number of ways that BOINKS are being used in therapy:

for in-hand manipulation in order to develop the radial side of the hand for strengthening and developing functional grasping patterns;

for developing bilateral coordination and supination by placing the braided mesh tube in the palm of one hand and shooting it upward with the other;

for visual-motor games by shooting them at targets, as well as shooting up in the air and catching;

for self-regulation and attention to ameliorate fidgeting;

for children with Autism to engage them in play activities, and joint attention.

In summary, the flexible finger splint has been found to (1) elongate the finger, (2) stimulate tactile input, (3) compress without constriction, (4) useful for those with a Tonic Hand, as it is more comfortable than the hard plastic splints now on market. It has also been found that the flexible finger splint acts like an exoskeleton and acts like a muscle. Further, the flexible finger splint is hypertonic so when in use and the finger is bent, it will spring back into the neutral position. The flexible finger splint helps if there is swelling in the hand. One can massage the hand, to get the swelling down, and then slide the flexible finger splint over the affected finger. It will compress and delay the swelling to return. The finger splint helps with Gradient Compression. It helps to amplify what the patient sees when they are bending finger. It protects the distal phalanx and extends the DIP joint and it encourages more movement with positive reinforcement A number of aspects and embodiments of the invention have been described. It is to be understood that various modifications may be made without departing from the spirit and scope of the invention.

I claim:
1. A method of supporting a finger comprising the steps of:
providing a finger splint, the finger splint comprising:
a braided mesh folded over itself to form a hollow tube having a double wall and having a longitudinal axis,
the folded over braided mesh having a first open end that is flared;
wherein the hollow tube is compressible and after being compressed and released, springs back to its original shape; and
inserting a finger into the first open end of the finger splint.

2. The method of claim 1, wherein the open end is an end where the splint has been folded over.

3. The method of claim 1, wherein the open end is flared.

4. A method of rehabilitating a finger comprising the steps of:
providing a finger splint, the finger splint comprising:
a braided mesh folded over itself to form a hollow tube having a double wall and having a longitudinal axis,
the folded over braided mesh having a first open end that is flared;
wherein the hollow tube is compressible and after being compressed and released, springs back to its original shape;
inserting a finger into the first open end of the finger splint; and
changing the shape of the finger splint by making grasping motions with the finger.

5. The finger splint of claim 4 wherein the braid is made of a textile composition made with yarn thread crossing in diagonal direction, wherein each thread intertwines the diagonal threads it crosses, one from above and one from below.

6. The finger splint of claim 4, wherein the mesh is PET.

* * * * *